United States Patent [19]
Apffel et al.

[11] Patent Number: 5,705,813
[45] Date of Patent: Jan. 6, 1998

[54] INTEGRATED PLANAR LIQUID HANDLING SYSTEM FOR MALDI-TOF MS

[75] Inventors: James A. Apffel, Palo Alto; John A. Chakel, San Mateo; William S. Hancock, Hillsborough; Kay Lichtenwalter, San Jose, all of Calif.

[73] Assignee: Hewlett-Packard Company, Palo Alto, Calif.

[21] Appl. No.: 548,349

[22] Filed: Nov. 1, 1995

[51] Int. Cl.⁶ .................................................. H01J 49/04
[52] U.S. Cl. ................................................... 250/288
[58] Field of Search .............................. 250/288, 288 A, 250/281, 282

[56] References Cited

U.S. PATENT DOCUMENTS

| | | | |
|---|---|---|---|
| 4,891,120 | 1/1990 | Sethi et al. | 204/299 R |
| 4,908,112 | 3/1990 | Pace | 204/299 R |
| 5,132,012 | 7/1992 | Miura et al. | 210/198.2 |
| 5,194,133 | 3/1993 | Clark et al. | 204/299 R |
| 5,481,110 | 1/1996 | Krishnaswamy et al. | 250/288 |

FOREIGN PATENT DOCUMENTS

WO94/28418  5/1994  WIPO ................. 33/543

OTHER PUBLICATIONS

Bai et al., "Peptide Mapping by CNBr Degradation on a Nitrocellulose Membrane with Analysis by Matrix–Assisted Laser Desorption/Ionization Mass Spectrometry", Anal. Chem., vol. 67, pp. 1705–1710 (1995), no month.
Beavis and Chait, "High–Accuracy Molecular Mass Determination of Proteins Using Matrix–Assisted Laser Desorption Mass Spectrometry", Anal. Chem., vol. 62, pp. 1836–1840 (1990) no month.
Busch, K., "Mass Spectrometric Detectors for Samples Separated by Planar Electrophoresis", J. Chromatog. A, vol. 692, pp.275–290 (1995) no month.
Chait, et al., "Protein Ladder Sequencing", Science, vol. 262, pp. 89–92 (1993) no month.

de Frutos et al., "Liquid Chromatography Based Enzyme–Amplified Immunological Assays in Fused–Silica Capillaries at the Zeptomole Level", Anal. Chem., vol. 65, pp. 2159–2163 (1993) no month.
Jacobson et al., "Effects of Injection Schemes and Column Geometry on the Performance of Microchip Electrophoresis Devices", Anal. Chem., vol. 66, pp. 1107–1113 (1994) no month.
Liu et al., "Rapid Screening of Genetic Polymorphisms Using Buccal Cell DNA with Detection by Matrix–assisted Laser Desorption/Ionization Mass Spectrometry", Rapid Commun. Mass Spec., vol. 9, pp. 735–743 (1995) no month.
Manz et al., "Planar Chips Technology for Miniaturization of Separation Systems: A Developing Perspective in Chemical Monitoring", Advances in Chromatography, vol. 33, pp. 1–66 (1993) no month.
Schöneich et al., "Separation and Analysis of Peptides and Proteins", Anal. Chem. vol. 65, No. 12, 67R–84R (1993) no month.
Tang et al., "Matrix–assisted Laser Desorption/Ionization Mass Spectrometry of Immobilized Duplex DNA Probes", Nucleic Acids Res., vol. 23, No. 16, pp. 3126–3131 (1995) no month.
Wu and Regnier, "Native Protein Separations and Enzyme Microassays by Capillary Zone and Gel Electrophoresis", Anal. Chem., vol. 65, pp. 2029–2035 (1993) no month.

*Primary Examiner*—Kiet T. Nguyen
*Attorney, Agent, or Firm*—Susan J. Friedman

[57] ABSTRACT

An integrated liquid sample handling system for matrix-assisted laser-desorption/ionization time-of-flight mass spectroscopy (MALDI-TF MS) is described. The integrated system comprises a miniaturized sample handling compartment containing a MALDI ionization surface for separating, chemically manipulating and detecting analytes by MALDI -TOF MS. The miniaturized integrated sample handling system disclosed herein is applicable to a wide range of analytical problems that require separation and/or chemical manipulation of a sample prior to mass analysis as part of the analytical procedure.

9 Claims, 5 Drawing Sheets

INTEGRATED PLANAR LIQUID HANDLING SYSTEM FOR MALDI-TOF MS

TECHNICAL FIELD

The present invention relates generally to sample preparation for mass spectroscopy. More particularly, the invention relates to a miniaturized integrated liquid sample handling system for matrix-assisted laser-desorption/ionization time-of-flight mass spectroscopy (MALDI-TOF). The integrated system disclosed herein is applicable to a wide range of bioanalytical problems that require chemical manipulation prior to mass analysis as part of the analytical procedure.

BACKGROUND

The sensitivity, mass range and ability to analyze complex mixtures has made mass spectrometry an important tool for the analysis of large biomolecules. The recent employment of matrix-assisted-laser-desorption/ionization (MALDI) (Karas & Hillenkamp, Anal. Chem. 60, 2299 (1988)) with time-of-flight (TOF) mass spectrometry has extended the mass range and accuracy of mass spectrometric measurements to include proteins and nucleic acids. See generally, Kinter, Anal. Chem. 67, 493R–497R (1995); Schoneich et al, Anal. Chem. 67, 155R–181R (1995); Busch, J. Chromatog. A 692, 275–290 (1995); and Limbach et al, Curr. Opin. Biotechnol. 6, 96–102 (1995).

Because of its high sensitivity and relatively high tolerance to the presence of contaminants in the sample compared with ESI (electrospray ionization), MALDI MS is increasingly used in biotechnological and pharmaceutical areas to provide amino acid residue-specific and sequence information about protein products produced by recombinant techniques and for use in gene cloning. For example, this technique has been used to measure the mass of subpicomole amounts of intact polypeptide chains with a mass accuracy of up to 1 part in 10,000 (Beavis & Chait, Anal. Chem. 62, 1836 (1990)), for peptide mapping (Bai et al, Anal. Chem. 67, 1705–1710 (1995); for sequencing proteins and peptides (Chait et al, Science 262, 89–92 (1993); and for detecting posttranslational modifications (W. T. Hutchens, PCT application, WO 94/28418).

With increasing recognition of the biological and biomedical importance of protein sequence variations, covalent modifications, and microheterogeneities introduced during synthesis, processing, and degradation of proteins in vivo, there is a corresponding need to improve methods of detection and characterization of these changes. Multiple biochemical techniques are required to solve these subtle structural problems. Where only submicromolar amounts of proteins are available, special sample handling and preparation techniques are required. The ability to automate procedures and reduce the amount of sample handling is of particular interest in this regard. With this in mind, miniaturized separation systems are being developed for use in total analysis systems.

In using MALDI mass spectrometry as a tool for structure determination, there is a need to replace the widespread current practice of off-line sample preparation and separation with a miniaturized sample handling system that is integrated with MALDI MS detection means. An integrated miniaturized sample handling system capable of automation is expected to minimize the potential for loss of sample and sample contamination and to increase the reproducibility and speed of analysis.

SUMMARY OF THE INVENTION

To address the above-mentioned need in the art, the invention disclosed and claimed herein provides an integrated liquid handling system for MALDI-TOF MS in a thin film support, wherein the system is comprised of a miniaturized sample handler integrated with a MALDI ionization surface for detection and measurement of analytes in a time-of-flight mass spectrometer.

It is an object of the present invention to provide an automatable device for improved sample handling prior to mass spectrometric analysis. A miniaturized system according to the present invention is capable of performing complex sample handling, separation and sample presentation for measurement with speed and precision without the need for significant manual manipulation and interaction.

It is yet another object of the present invention to enable the handling of small amounts of sample with minimal sample loss. A miniaturized sample handling compartment having automatable means for separating, chemically manipulating and moving analytes from point to point within the compartment greatly reduces the likelihood of sample loss.

It is a related object of the present invention to increase the sensitivity and selectivity of analyte measurement by providing a capture region and/or separation means within the sample handling compartment for concentrating an analyte present in low concentration in the sample and for removing potentially interfering molecules and ions from the analyte sample prior to mass spectrometry, thereby increasing the signal intensity and decreasing the noise in the mass spectrum.

It is yet a further related object of the present invention to reduce the cost of molecular analysis by mass spectroscopy by constructing the liquid handling system as a single disposable unit.

DETAILED DESCRIPTION OF THE INVENTION

Before the invention is described in detail, it is to be understood that this invention is not limited to the particular component parts of the device described or process steps of the methods described, as such devices and methods may vary. It is also to be understood that the terminology used herein is for purposes of describing particular embodiments only, and is not intended to be limiting. As used in the specification and the appended claims, the singular forms "a", "an", and "the" include plural referents unless the context clearly indicates otherwise. Thus, for example, reference to "an analyte" includes mixtures of analytes, reference to "a MALDI ionization surface" includes two or more such ionization surfaces, reference to "a microchannel" includes more than one such component, and the like.

In this specification and in the claims which follow, reference will be made to a number of terms which shall be defined to have the following meanings:

The terms "analyte" and "analyte sample" are used interchangeably herein to refer to one or a mixture of molecules (or portions thereof) whose mass is to be measured by the technique of MALDI-TOF MS. The analyte may be present in the initial sample or may instead be generated de novo within the sample handling region (e.g., the product of an enzymatic or chemical reaction). An analyte can be obtained from biological fluids, cell or tissue extracts, fermentation broths, food stuffs, microorganisms, viruses, plants, environmental materials and the like, or may originate by synthetic, semi-synthetic or other processes not found in nature (e.g., by combinatorial synthesis). Prior to analysis, an analyte may require amplification, covalent modification, concentration or separation from other analytes or non-analyte molecules and ions in the sample handling compartment.

The term "analysis" as used herein refers to the application of MALDI-TOF MS for mass determination and/or structure elucidation of an analyte.

The terms "analyte-binding partner" or "analyte capture molecule" are used interchangeably herein to refer to molecules that recognize general physicochemical characteristics of the "target analyte" (e.g., hydrophobic domain or hydrophilic surface of a protein, strandedness of a nucleic acid) or specific chemical features (e.g., amino acids, sugars or nucleotide sequences). Binding partners may include binding proteins or portions thereof (e.g. binding proteins for receptors, hormones, vitamins, etc.), peptides, biomimetic molecules (e.g. flexible polymeric ion-exchangers), oligonucleotides and oligonucleotide analogs, lectins, and the like. Any of the aforementioned types of "analyte-binding partners" can be used in the present invention if they possess a sufficiently high binding affinity and selectivity for the target analyte to permit the invention to be practiced.

The term "MALDI" is used herein to refer to Matrix-Assisted Laser Desorption/Ionization, a process wherein analyte is embedded in a solid or crystalline "matrix" of laser light-absorbing molecules (e.g., nicotinic, sinapinic, or 3-hydroxypicolinic acid), then desorbed by laser irradiation and ionized from the solid phase into the gaseous or vapor phase, and accelerated as intact molecular ions towards a detector. The "matrix" is typically a small organic acid mixed in solution with the analyte in a 10,000:1 molar ratio of matrix/analyte. The matrix solution can be adjusted to neutral pH before mixing with analyte.

The term "MALDI-TOF MS" is used herein to refer to Matrix-Assisted Laser Desorption/Ionization Time-of-Fight mass spectrometry.

Figure 1:
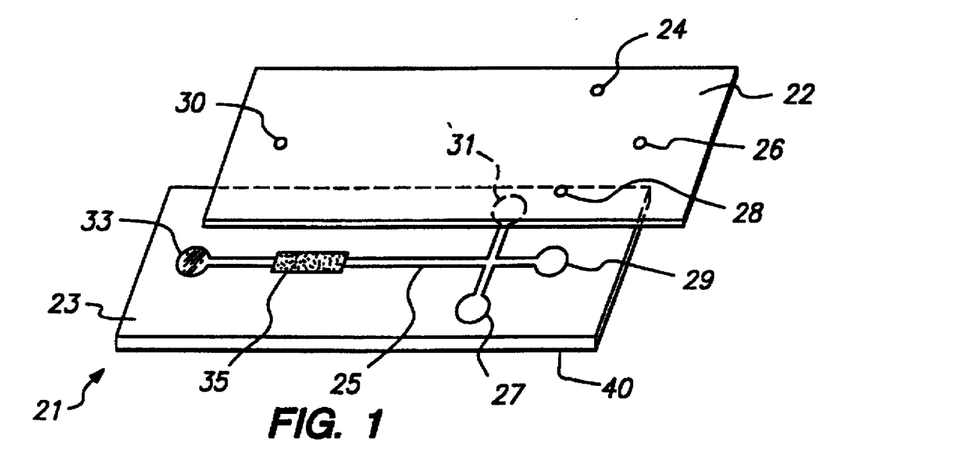
FIG. 1 is an exploded view of an embodiment of an integrated liquid handling system for MALDI-TOF MS.
Figure 2A:
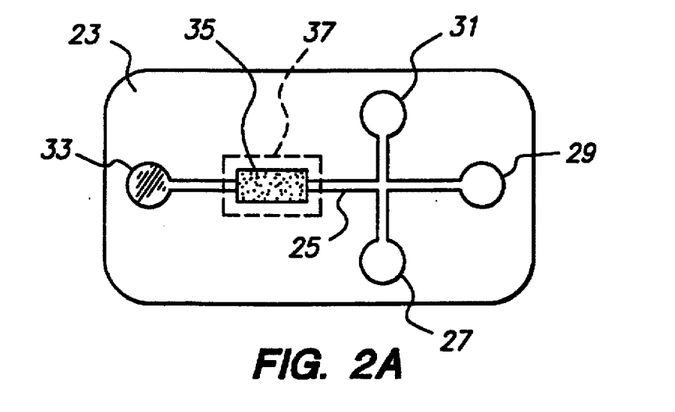
FIG 2A is a plan view of the upper surface (panel A) of the embodiment shown in FIG. 1.
Figure 2B:
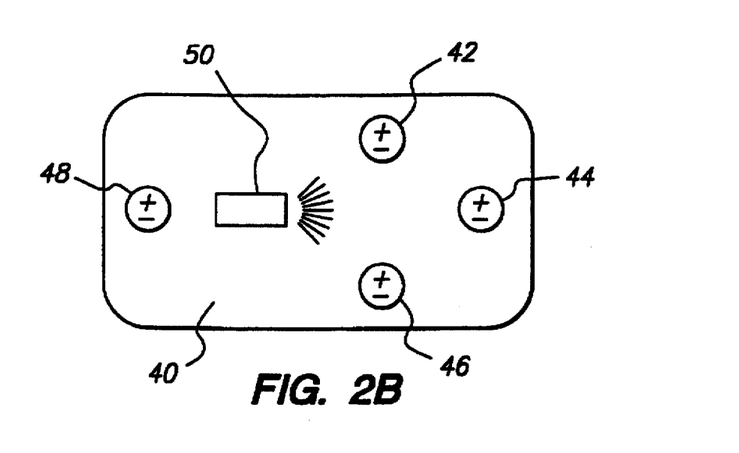
FIG 2B is a plan view of the lower surface (panel B) of the embodiment shown in FIG. 1.
Figure 3:
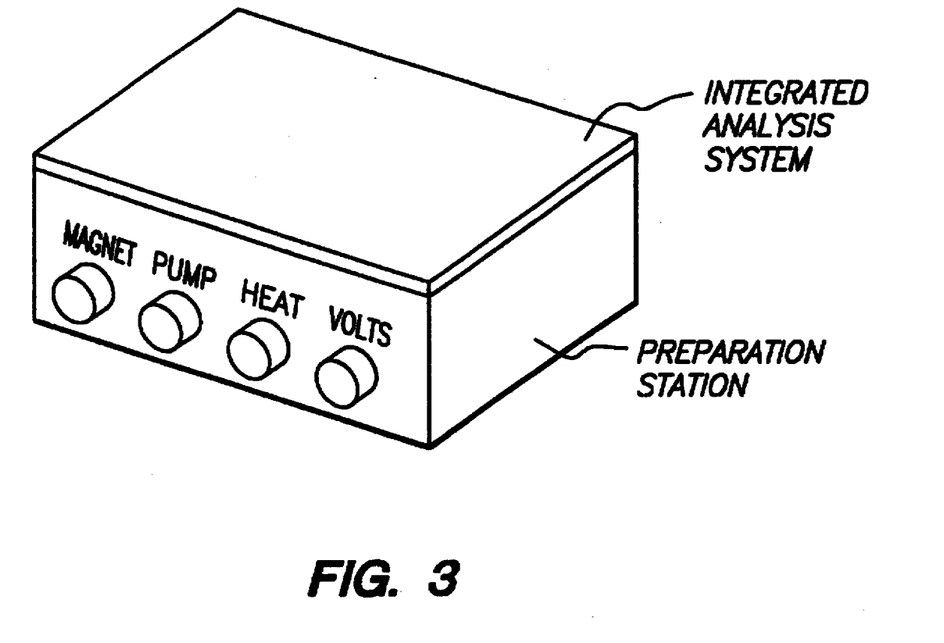
FIG. 3 illustrates a preparation station interfaced with an integrated liquid handling system.

Referring now to FIGS. 1, 2A and 2B, the term "thin film support" is used to refer to a substantially planar miniature manifold 21 made of a non-conducting material having an upper surface 23 and a lower surface 40. A sample handling compartment defined in the upper surface 23 includes a microchannel 25, one or more reservoirs 27, 29 and 31 for receiving fluid substances involved in sample handling and a MALDI ionization surface 33. The lower surface 40 is provided with means 42, 44, 46 and 48 for moving an analyte and fluids within the compartment. The means 42, 44, 46 and 48 may be, for example, electrical connections for producing voltage gradients at desired locations of the sample handling compartment. The lower surface 40 is also provided with means 50 such as a peltier surface for controlling the temperature of desired regions of the sample handling compartment. A preparation station as depicted in FIG. 3 is preferably used to supply electricity, heat, pressure and magnetization to the sample handling compartment. Such a miniaturized device may be formed from a variety of materials (e.g., silicon, glass, low cost polymers) by techniques that are well-known in the art (e.g., micromachining, chemical etching, laser ablation, and the like). Portions of the device may be fabricated from composite materials. For example, a thermally insulated reaction zone may be formed from bonded layers of materials having different thermal conductivities. Established techniques exist for micromachining planar materials such as silicon and provide a useful and well-accepted approach to miniaturization. Examples of the use of such micromachining techniques to produce miniaturized separation devices on silicon or borosilicate glass chips can be found in U.S. Pat. No. 5,194,133 to Clark et at; U.S. Pat. No. 5,132,012 to Miura et at, U.S. Pat. No. 4,908,112 to Pace; and in U.S. Pat. No. 4,891,120 to Sethi et at.

The term "sample handling compartment" is used herein to refer to a region of the support where all procedures necessary to prepare an analyte for mass spectrometry are carried out. Such procedures may include but are not limited to: concentrating an analyte from a dilute solution (e.g. by selective absorption to a chemically-modified surface); separating multiple analytes in a mixture or separating one or more analytes from impurities (e.g., by chromatographic and/or electrophoretic procedures); performing ion exchange or buffer exchange on an analyte-containing fluid; carrying out chemical reactions on an analyte (e.g., derivatization-tagging to improve detection sensitivity or specificity, chemical or enzymatic digestions to facilitate identification or structural analysis of the analyte), enzymatically generating an analyte de novo (e.g., for enzyme-linked immunoabsorbent assay, analysis of covalent modifications of proteins and oligonucleotides, enzyme kinetic studies). The sample handling compartment frequently will include one or more access ports for introducing materials into, and withdrawing materials from the compartment (e.g., introduction of sample and reagents, flushing the compartment or a region thereof with fluid from an external reservoir). As shown in FIG. 1, access ports 24, 26, 28 and 30 may be provided in a cover 22 if its desired to enclose the upper surface of the thin film support.

The term "separation region" is used herein to refer to a region of the sample handling compartment where electrophoretic and chromatographic separations are carried out.

Descriptions of technologies involved in miniaturizing separation systems and the use of these systems for separating both large and small molecules are given by Manz et al, "Planar Chips Technology for Miniaturization of Separation Systems: A Developing Perspective in Chemical Monitoring", In *Advances in Chromatography* (Brown, P. R. & Grushka, E. Eds.), 1993, pp 1–66; Schöneich et al, Anal. Chem.67, 155R–181R (1995): proteins; Xu, ibid, pp. 463R–473R: drugs and enzymes; Woolley & Mathies, Proc. Natl. Acad. Sci. USA 91, 11348–11352 (1994): DNA; de Frutos et al, Anal. Chem. 65, 2159–2163 (1993); and Wu & Regnier, Anal. Chem. 65, 2029–2035 (1993); enzyme assays.

The separation regions are formed within microchannels or portions thereof, the surfaces of which are treated for biocompatibility with the analyte sample (i.e. to protect the analyte from undesired structure or activity changes upon contact with the microchannel surface), and for controlling electroosmotic flow and non-specific protein adsorption. Such treatments may be dynamic or static in nature as appropriate for the intended analytical application (See, e.g., Schöneich et al, Anal. Chem. 65:67R–84R (1993) for a detailed description of procedures that have been used in the art).

For chromatographic-type separations, the microchannel separation regions are coated with chromatographic matrices (e.g., various stationary phases for HPLC; various ligands for affinity chromatography) according to methods known in the art. For certain electrophoretic applications, the use of gel-filled capillaries is advantageous. The preparation of cross-linked and linear hydrophilic polymer gels in microcapillaries is described in references cited by Sch öneich et al (above). A single sample handler may contain a plurality of separation channels with different separation modes.

The term "reaction zone" is used herein to refer to a microenvironment within the sample handling compartment for carrying out chemical and enzymatic reactions on an analyte. Therefore, as shown in FIGS. 1 and 2A, the reaction zone comprises a region 35 that is capable of spatially restricting reactants (e.g., reagents, catalysts, substrates) for a sufficient time to allow the intended reaction to occur. It is useful and often essential to maintain a uniform and constant temperature within a reaction zone. Thus it is contemplated that the sample handling compartment will include temperature controlling devices 50, as shown in FIG 2B (e.g., sensors, thermocouples, heaters) and adequate thermal insulation 37, as shown in FIG. 2A of a reaction zone to prevent unintended cross-heating of other regions of the compartment. Typically, the reaction zones of this invention are temperature-controlled over the range of about 10° C. to about 100° C.

According to the present invention, a reaction zone may be formed in a microchannel, a MALDI ionization surface or another microstructure in the sample handling compartment. Spatial restriction of the reaction within a microchannel may be accomplished by various methods, e.g., physical immobilization of an analyte, analyte binding partner, or catalyst on the microchannel surface (described below under "capture region"), or confinement of soluble reactants by controlling their movement into and out of the channel (e.g., see Wu & Regnier, Anal. Chem. 65, 2029–2035 (1993): use of zero- or constant-potential conditions for electrophoretically mediated enzyme assays; de Frutos et al, Anal. Chem. 65, 2159–2163 (1993): stopped flow immunological assays).

A plurality of reaction zones may be provided within the same sample handling compartment for carrying out simultaneous reactions under the same or different reaction conditions, for successive chemical manipulations of an analyte (e.g., removal of posttranslational modifications from a polypeptide and peptide mapping), for analysis of complex analyte mixtures, and the like.

The term "capture region" is used herein to refer to a region or regions within the sample handling compartment wherein procedures that require immobilization of the analyte can be performed (e.g., concentration of analyte from a dilute solution, removal of potentially interfering molecules and ions initially present in the sample or introduced during analyte handling, buffer exchange, and the like).

Capture regions may be formed by well-known methods for attaching affinity ligands to solid supports. See, generally, *Affinity Techniques. Enzyme Purification: Part B. Methods in Enzymology*, Vol. 34, (Jakoby, W. B. & Wilchek, M., Eds.) Acad. Press, NY (1974) and *Immobilized Biochemicals and Affinity Chromatography, Advances in Experimental Medicine and Biology*, Vol. 42, (Dunlap, R., Ed.) Plenum Press, NY (1974), which are incorporated herein by reference. For example, the surface of a bead, particle or planar support can be treated with a bifunctional cross-linking reagent (i.e., a cross-linking reagent having the same or different chemical reactivities on each end of a molecular linker) to attach one end of the reagent to reactive groups on the surface, and the opposite end to an analyte binding partner. The cross linker is preferably of sufficient length to permit the attached analyte binding partner to interact freely with compounds in solution. Crosslinking groups may be attached to the surface by siloxane bonds using organosilanes such as such as 3-glycidoxypropyltrimethoxysilane ("GOPS"), 3-aminopropyltriethoxysilane (APS), and the like, which have well-understood chemistries. Another preferred method for immobilizing analyte binding partners on surfaces is to covalently link avidin or streptavidin to the surface, and subsequently to react the surface with an analyte binding partner that has been covalently bound to biotin or a biotin analog. Avidin and streptavidin bind biotin noncovalently but with very high affinity (the $K_a$ is approximately $10^{15}$ $M^{-1}$. See Green, "Avidin" in *Advances in Protein Chemistry*, Academic Press, vol. 29, 105 (1975). Biotinylated biopolymers can be prepared as described in the literature. See e.g., Bayer et al., *Methods of Biochemical Analysis*, Vol. 26 (Glick, D., Ed.), 1–45 (1980), and Current Protocols in *Molecular Biology*, Supplement 20 (John Wiley & Sons, Inc.), which are incorporated herein by reference.

According to the practice of the present invention, a capture region may be formed in any microstructure in the sample handling compartment by anchoring the analyte binding partner to the microstructure surface directly or via a second docking structure (e.g., bead, particle, gel, membrane) on which the analyte binding partner is tethered. Immobilization of the analyte binding partner or docking structure may, for example, be by chemical, magnetic, or electrical means depending on the needs of the user, the properties of the analyte and analyte binding partner, and/or the nature of the docking structure.

In addition to affinity capture methods, which are preferred for the practice of the present invention, analyte capture can be effectuated by hydrophobic or charge interactions, or by chelational mechanisms.

A captured analyte may be released into solution by various methods known in the art to dissociate high affinity binding mediated by hydrogen bonds, electrostatic, hydrophobic and polar interactions or a combination thereof (e.g., changing temperature, pH, solvent polarity, using chaotropic salts, localized heating with laser irradiation, and the like). Changes in electric field strength can be used to disrupt electrostatic binding. An analyte captured on a magnetically responsive particle can be mobilized by altering the magnetic field strength.

The term "MALDI ionization surface" is used herein to refer to a surface for presentation of matrix-embedded analyte into a mass spectrometer for MALDI. In general, the terms "probe" or "probe element" are used interchangeably to refer to a device for presenting analyte into a mass spectrometer for irradiation and desorption.

The ionization surface may be composed of an inert material or else modified to actively capture an analyte. For example, an analyte binding partner may be bound to the surface to selectively absorb a target analyte or the surface may be coated with a thin nitrocellulose film for nonselective binding to the analyte. The surface may also be used as a reaction zone upon which the analyte is chemically modified, e.g., CNBr degradation of protein. See Bai et al, Anal. Chem. 67, 1705–1710 (1995).

Metals such as gold, copper and stainless steel are typically used to form MALDI ionization surfaces. However, other commercially-available inert materials (e.g., glass, silica, nylon and other synthetic polymers, agarose and other carbohydrate polymers, and plastics) can be used where it is desired to use the surface as a capture region or reaction zone. The use of Nation and nitrocellulose-coated MALDI probes for on-probe purification of PCR-amplified gene sequences is described by Liu et at, Rapid Commun. Mass Spec. 9:735–743 (1995). Tang et al have reported the attachment of purified oligonucleotides to beads, the tethering of beads to a probe element, and the use of this technique to capture a complimentary DNA sequence for analysis by MALDI-TOF MS (reported by K. Tang et at, at the May 1995 TOF-MS workshop, R. J. Cotter (Chairperson); K. Tang et al, Nucleic Acids Res. 23, 3126–3131, 1995). Alternatively, the MALDI surface may be electrically- or magnetically activated to capture charged analytes and analytes anchored to magnetic beads respectively.

The term "amplification" is used herein to refer to any in vitro method for increasing the copy number of a target nucleic acid sequence. It is also used to refer to the increase in amount of an analyte reporter molecule, e.g., the reaction product of an enzyme attached to the analyte or to an anti-analyte antibody.

The term "PCR" is used herein to refer to the polymerase chain reaction (PCR).

The term "transparent" is used herein to refer to the ability of a material to transmit light of different wavelengths, which ability may be measured as the percent of radiation which penetrates a distance of 1 meter. For example, in the present invention, the upper surface of the sample handling compartment is preferably transparent to allow microscopic observation of sample handling, if desired, and to facilitate laser irradiation of the sample preparation compartment, when necessary.

The terms "chromatographic separation" and "chromatography" are used herein to refer to preferential separations of components based on their differential partitioning between mobile and stationary phases, e.g., reversed-phase, hydrophobic interaction, ion exchange, molecular sieve, and like methods.

The terms "electrophoretic separation" and "electrophoresis" are used herein to refer to separations based on differential migration of charged components in an electric field.

The term "electrochromatographic separation" and "electrochromatography" refers to combinations of electrophoretic and chromatographic techniques (e.g., micellar electrophoretic separation, Terabe et al, Anal. Chem. 57, 834–841, 1985).

The term "electroosmosis" and "electroosmotic flow" is used herein to refer to the electrically-driven movement of a conducting liquid. In the present invention, a charged surface of a microstructure will attract counterions present in the liquid thus forming a diffuse double layer of ions. Under an external electric field, the net movement of counterions towards the oppositely charged electrodes will cause the fluid to move in the same direction.

"Optional" or "optionally" means that the subsequently described feature or structure may or may not be present in the analysis system or that the subsequently described event or circumstance may or may not occur, and that the description includes instances where said feature or structure is present and instances where the feature or structure is absent, or instances where the event or circumstance occurs and instances where it does not. For example, the phrase "optionally enclosed upper surface" means that the upper surface may or may not be enclosed and that the description includes both circumstances where the enclosure is present and absent.

The term "vacuum gate" is used herein to refer to an opening in the vacuum chamber of a mass spectrometer into which the MALDI ionization surface is inserted.

The invention provides an integrated liquid handling system for MALDI-TOF MS in a thin film support, wherein the system is comprised of a miniature sample handler integrated with a MALDI ionization surface for detection and measurement of analytes in a time-of-flight spectrometer.

An integrated planar liquid handling system for MALDI-TOF MS can be constructed in single low cost consumable unit formed predominantly from a nonconducting material such as glass, silicon, or a low-cost plastic polymer. The unit can include microchannels, reaction zones for carrying out chemical and enzymatic reactions, interfaces to non-consumable parts, and an ionization surface for MALDI-TOF MS. Using emerging technologies found in micromachining and nanotechnology, low cost thin film supports can be etched with microchannels, mixing chambers, wells, and valves to allow an analyte to be introduced, moved through a series of chemical manipulations which are spatially (and therefore temporally) separated, and deposited on a MALDI ionization surface interfaced with a mass spectrometer. The entire sequence of steps from sample introduction to sample detection is capable of being automated.

The advantage of integrating the sample handling compartment with the MALDI ionization surface is to allow automated chemical manipulation and/or separation of analytical samples prior to analysis by MALDI-TOF MS for enhanced selectivity, sensitivity and reproducibility of the measurements with reduced contamination and sample loss. This feature is of particular importance for achieving the full sensitivity of MALDI-TOF.

In the practice of the invention, fluids and analytes can be introduced into, and moved from point to point within, the sample handling compartment by applying voltage gradients at desired locations whereby analytes are transported by electrokinesis or electroosmosis. Hydrodynamic flow means and other procedures for creating localized pressure changes are also used in miniaturized separation devices. Electrophoretic methods are available for precise low-volume sample injections (see, e.g., Woolley & Mathies, Proc. Natl. Acad. Sci. USA 91, 11348–11352 (1994) and Jacobson et al, Anal. Chem. 66, 1107–1113 (1994)). Reactants can be mixed electrophoretically or hydrodynamically prior or subsequent to entry into a reaction zone.

Electrostacking procedures known in the art can be used to concentrate ionic analytes in the sample prior to introduction into a sample handling compartment and for stacking separated analytes within a MALDI ionization surface. Uncharged analytes can be concentrated for sample handling and detection by means of capture regions. It should be noted that one skilled in the art will know of other methods that can be used for the described purposes.

Unless otherwise indicated, the practice of the present invention will employ conventional techniques of analytical and organic chemistry, molecular biology, protein chemistry, immunology, and recombinant DNA technology which are within the skill of the art. These techniques are fully explained in the literature. See, e.g., the series, *Methods in Enzymology* (Colowick S. and Kaplan, N. Eds., Acad. Press, Inc.), *Current Protocols in Molecular Biology* (John Wiley & Sons, Inc.), Keller & Manak, *DNA Probes*, 2nd Ed., (Stockton Press, 1993), *Antibodies: a Laboratory Manual*, Harlow E. & Lane, D. (Cold Spring Harbor Laboratory, 1988) which are incorporated herein by reference.

Several useful applications of the present invention are depicted below in FIGS. 4 through 6. These examples are intended to provide those of ordinary skill in the art with a description of how to use the invention and are not intended to limit the scope of what the inventors regard as their invention.

Figure 4:
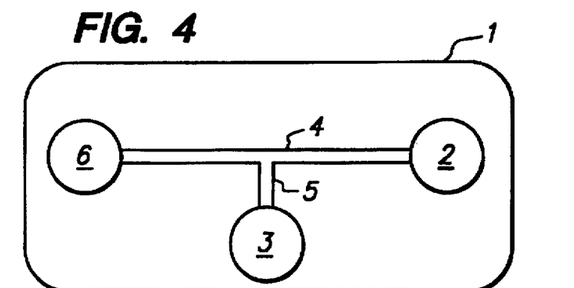
FIG. 4 illustrates the use of the present invention for electrophoretic desalting of an analyte.
Figure 4A:
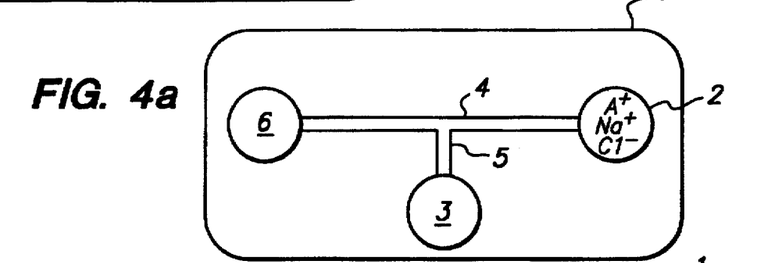
Figure 4B:
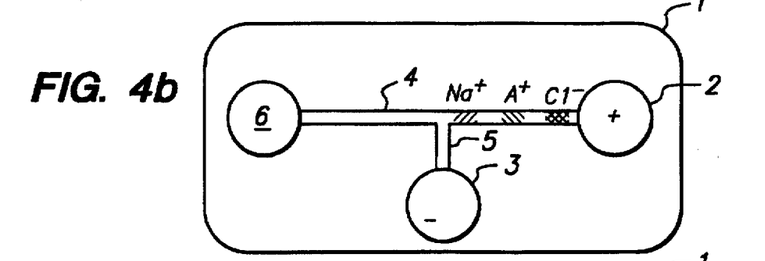
Figure 4C:
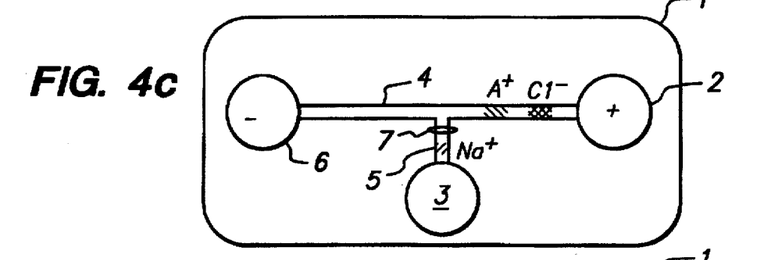
Figure 4D:
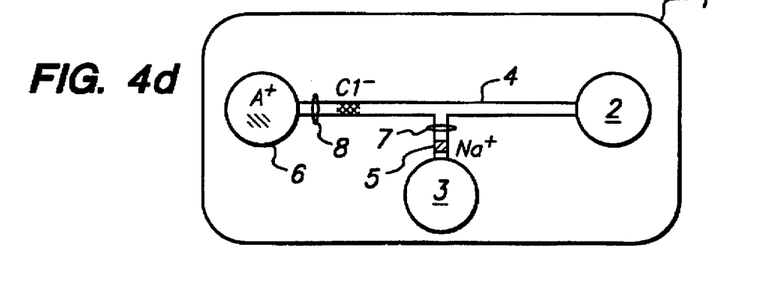

The use of the present invention for electrophoretic desalting of an analyte is shown in panels (a) through (d) of FIG. 4. Assume that the sample contains a protein analyte in a buffer containing a high concentration of NaCl which may interfere with the MALDI-TOF MS analysis. The sample is introduced into a sample reservoir (2) in the substantially planar thin film support (indicated generally at 1)(panel (a)). A voltage is applied between the sample reservoir (2) and waste reservoir (3) panel (b)). The small, highly mobile $Na^+$ ions move in the microchannel (4) ahead of the protein analyte, $A^+$, while the $Cl^-$ ions lag behind (or, in the absence of electroosmosis, are retained at the anode). After the entry of the $Na^+$ ions (but before the entry of the protein analyte) into the waste microchannel (5), the cathode is switched to the MALDI ionization surface (6) and, if necessary, the waste channel is sealed (7) (panel (c)). The protein and more slowly moving $Cl^-$ ions then migrate to the MALDI ionization surface. When the protein has moved onto the MALDI ionization surface (panel(d)), the voltages are turned off and the MALDI microchannel is sealed (8), thereby effecting a desalting of the protein analyte. The MALDI matrix is added and the support is dried and transferred to the vacuum gate of the mass spectrometer for commencement of the MALDI experiment. As described above, the MALDI ionization surface may be modified for analyte capture to permit additional rinsing of the sample surface to remove unbound species. Following the measurement, the support is removed and discarded.

Figure 5:
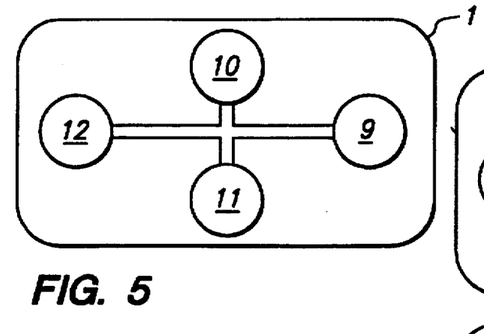
FIG. 5 illustrates the use of the present invention for sample derivatization.
Figure 5A:
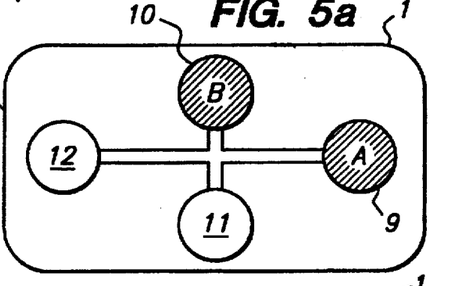
Figure 5B:
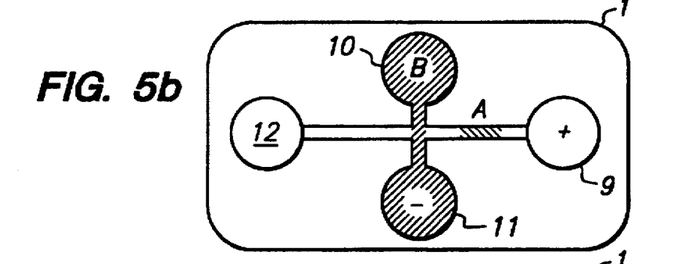
Figure 5C:
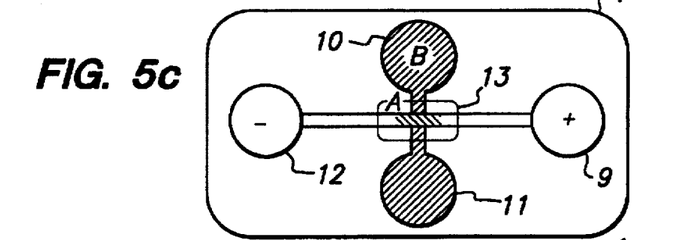
Figure 5D:
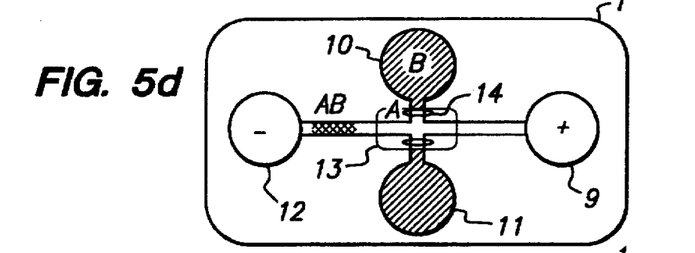
Figure 5E:
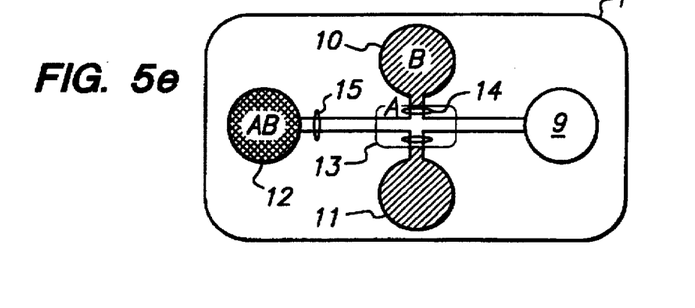

The panel (a) through of FIG. 5 illustrates the use of the present invention for sample derivatization to enhance the sensitivity or selectivity of MALDI analysis. Assume for example that an analyte of interest, A, is present in a mixture of analytes differing only slightly in mass, and that A is selectively capable of being derivatized with a particular chemical tag such that the mass of the tagged analyte is increased relative to the underivatized analytes in the sample. The sample is introduced to the sample reservoir (9) in the thin film support (panel (a)). The reagent, B, can either be prepackaged in or added to the reagent reservoir (10). A voltage is then applied between the sample reservoir and waste reservoir (11) thereby moving both the analyte and reagent electroosmotically and/or electrophoretically towards the waste reservoir (panel (b)). The reagent, present in large excess, will fill the reagent and waste reservoirs and the channel between them.

When the sample zone reaches the reagent zone (panel c)), the voltages can be turned off and the reaction can be carried out under zero potential conditions. Alternatively, the voltages can be turned on and off reversing the anode and cathode between the MALDI ionization surface (12) and sample reservoir to increase mixing during the reaction period. If heating is necessary to accelerate the reaction, peltier elements (13) can be positioned at the mixing region. The derivatized sample, AB, is then electrophoretically and/or electroosmotically moved to the MALDI ionization surface (panel (d)). If necessary, the channels to the reagent and waste reservoirs can be closed (14) to reduce reagent background. Finally, the MALDI ionization surface now containing the derivatized sample, AB, can be sealed off(15), the MALDI matrix can be added (if not already present), and the support dried for MALDI analysis (panel (e)).

Figure 6:
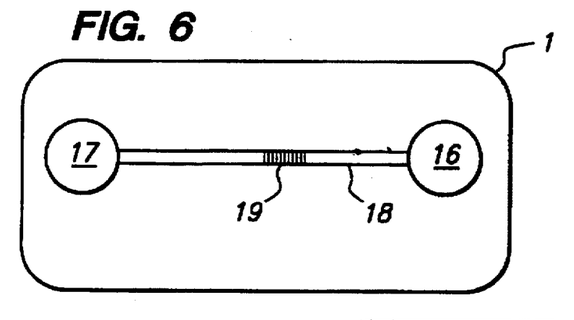
FIG. 6 illustrates the use of the present invention for enzymatic digestion of an analyte.
Figure 6A:
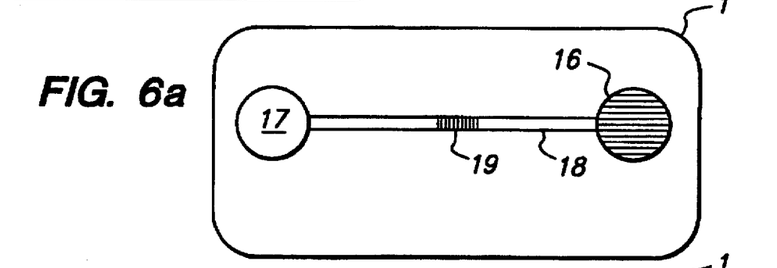
Figure 6B:
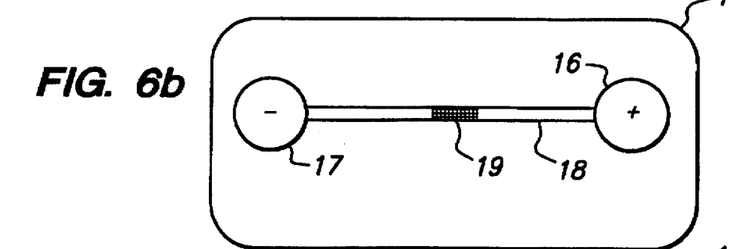
Figure 6C:
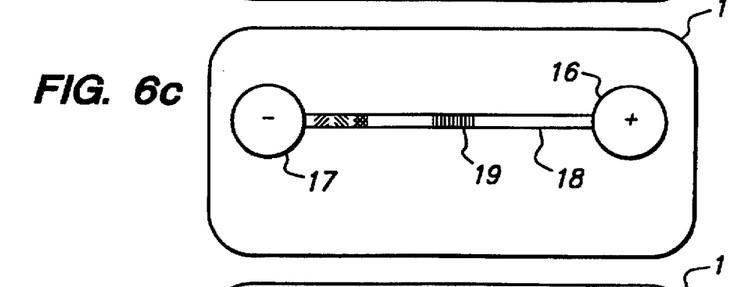
Figure 6D:
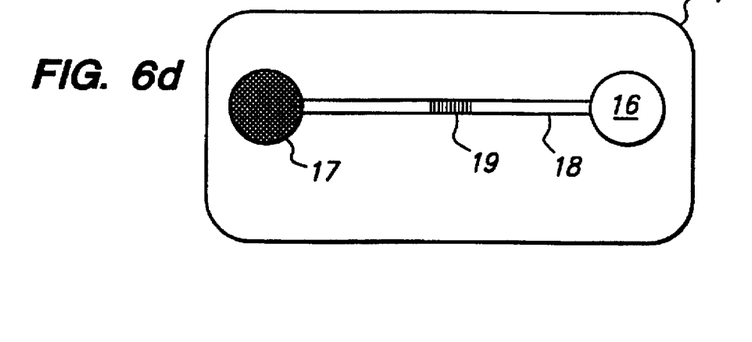

The use of the present invention for enzymatic digestion of a protein sample is exemplified in panels (a) through (d) of FIG. 6. In this particular embodiment, the thin film support contains a sample reservoir (16), a MALDI ionization surface (17) and an interconnecting microchannel (indicated generally at 18). A portion of the microchannel contains an immobilized enzyme (19). The enzyme can be immobilized on the surface of the channel or anchored to a particulate support. A particulate support would provide an increased surface area for mixing the sample and exposing it to enzyme. The sample is first introduced into the sample reservoir (panel (a)), moved electrophoretically to the immobilized enzyme zone (panel (b)) and allowed to react. Again, a peltier element (not shown) could be provided to increase the reaction temperature. The reaction products are electrophoretically moved from the immobilized enzyme zone towards the MALDI ionization surface panel (c)). After all of the fragments have reached the ionization surface (panel (d)), the surface can be isolated, matrix can be added (if not already present), and the support dried and presented for MALDI-TOF MS analysis. Variations of this procedure could include sequential collection and analysis of individual fragments or electrostacking of separating fragments onto the ionization surface to retain a certain degree of separation.

It is to be understood that while the invention has been described in conjunction with particular embodiments thereof, the description above and the embodiments shown in FIGS. 1 through 3 are intended to illustrate the invention and not to limit its scope. Other aspects, advantages and modifications within the scope of the invention will be apparent to those skilled in the art to which the invention pertains.

What is claimed is:

1. An integrated liquid handling system for a MALDI-TOF mass spectrometer comprising a thin film support having an upper surface and a lower surface, said upper surface including a sample handling compartment and said lower surface including means for moving an analyte and fluids within said compartment, wherein said sample handling compartment comprises:

a reservoir for receiving fluid substances;

a MALDI ionization surface; and a microchannel for interconnecting said reservoir and said ionization surface.

2. An integrated liquid handling system as in claim 1, wherein said microchannel comprises a separation region.

3. An integrated liquid handling system an in claim 2, wherein said separation region includes an analyte capture region for reversibly retaining said analyte from a contracting fluid mixture.

4. An integrated liquid handling system in claim 3, and further comprising means for heating the capture region.

5. An integrated liquid handling system as in claim 1 wherein said microchannel comprises a reaction zone for chemically manipulating said analyte, therein, and said reaction zone is temperature-controlled over a range of about 10° C. to about 100° C.

6. An integrated liquid handling system as in claim 1 further including: a preparation station for controllably inputting electricity, heat, pressure, and magnetization to said sample handling compartment responsive to momentary sample handling requirements; and means for interfacing said sample handling compartment and said preparation station.

7. An integrated liquid handling system as in claim 1, wherein said interconnecting microchannel includes reversible sealing means.

8. An integrated handling system as in claim 1, wherein said MALDI ionization surface includes a capture region.

9. An integrated liquid handling system as in claim 8, wherein said MALDI ionization surface further includes a reaction zone.

* * * * *